(12) United States Patent
Tomura et al.

(10) Patent No.: US 10,017,805 B2
(45) Date of Patent: Jul. 10, 2018

(54) ENHANCING INGREDIENTS FOR PROTEIN PRODUCTION FROM VARIOUS CELLS

(71) Applicants: Nissan Chemical Industries, Ltd., Tokyo (JP); Institute of National Colleges of Technology, Japan, Hachioji-shi (JP)

(72) Inventors: Misayo Tomura, Funabashi (JP); Takehisa Iwama, Funabashi (JP); Koichiro Saruhashi, Funabashi (JP); Taito Nishino, Shiraoka (JP); Masato Horikawa, Tokyo (JP); Hiroharu Kawahara, Kitakyushu (JP)

(73) Assignees: Nissan Chemical Industries, Ltd., Tokyo (JP); Institute of National Colleges of Tehcnology, Japan, Hachioji (JP)

( * ) Notice: Subject to any disclaimer, the term of this patent is extended or adjusted under 35 U.S.C. 154(b) by 0 days.

(21) Appl. No.: 13/974,820

(22) Filed: Aug. 23, 2013

(65) Prior Publication Data
US 2014/0162318 A1 Jun. 12, 2014

Related U.S. Application Data

(60) Provisional application No. 61/692,549, filed on Aug. 23, 2012.

(51) Int. Cl.
C12P 21/00 (2006.01)
C07K 14/565 (2006.01)
C12N 5/00 (2006.01)

(52) U.S. Cl.
CPC ............ *C12P 21/00* (2013.01); *C07K 14/565* (2013.01); *C12N 5/0018* (2013.01); *C12N 2501/90* (2013.01); *C12N 2511/00* (2013.01)

(58) Field of Classification Search
None
See application file for complete search history.

(56) References Cited

U.S. PATENT DOCUMENTS

| | | | |
|---|---|---|---|
| 5,968,501 A | 10/1999 | Comoglio | |
| 6,242,035 B1 * | 6/2001 | Clark | C08B 37/0024 426/573 |
| 6,284,451 B1 | 9/2001 | Funatsu et al. | |
| 8,609,377 B2 * | 12/2013 | Yang et al. | 435/101 |
| 2004/0091460 A1 | 5/2004 | Purcell et al. | |
| 2005/0084933 A1 | 4/2005 | Schilling et al. | |
| 2006/0121606 A1 | 6/2006 | Ito et al. | |
| 2006/0286627 A1 * | 12/2006 | Bochner | G01N 33/5023 435/40.5 |
| 2007/0074451 A1 | 4/2007 | Pearce et al. | |
| 2007/0292949 A1 | 12/2007 | Duguay et al. | |
| 2008/0070280 A1 | 3/2008 | Schilling et al. | |
| 2008/0145505 A1 | 6/2008 | Bezanson et al. | |
| 2008/0166751 A1 | 7/2008 | Asahara et al. | |
| 2009/0104141 A1 | 4/2009 | Ikeda et al. | |
| 2010/0145470 A1 | 6/2010 | Cohen et al. | |
| 2010/0178275 A1 | 7/2010 | Spanholtz | |
| 2011/0066111 A1 | 3/2011 | Teschner et al. | |
| 2011/0117061 A1 | 5/2011 | Zhang et al. | |
| 2011/0269232 A1 | 11/2011 | Takahashi et al. | |
| 2012/0087899 A1 | 4/2012 | Cool et al. | |
| 2012/0141975 A1 | 6/2012 | Sato et al. | |
| 2012/0213745 A1 | 8/2012 | Duguay et al. | |
| 2014/0106348 A1 | 4/2014 | Nishino et al. | |
| 2016/0060601 A1 | 3/2016 | Nishino et al. | |
| 2017/0175077 A1 | 6/2017 | Nishino et al. | |

FOREIGN PATENT DOCUMENTS

| | | |
|---|---|---|
| AL | 2138571 A1 | 4/2007 |
| CN | 102471762 A1 | 5/2004 |
| CN | 101591399 A | 12/2009 |
| CN | 101948815 A | 1/2011 |
| EP | 1576182 A2 | 9/2005 |
| EP | 2420563 A1 | 2/2012 |
| EP | 2878664 A1 | 6/2015 |
| JP | 62-171680 A | 7/1987 |
| JP | 63-209581 A | 8/1988 |
| JP | 07-107970 A | 4/1995 |
| JP | 08-023893 A | 1/1996 |
| JP | 08-140673 A | 6/1996 |
| JP | 11-187867 A | 7/1999 |
| JP | 2001-128660 A | 5/2001 |
| JP | 2004-236553 A | 8/2004 |
| JP | 2005-060570 A | 3/2005 |
| JP | 2006-076896 A | 3/2006 |
| JP | 2006-511224 A | 4/2006 |

(Continued)

OTHER PUBLICATIONS

Fan et al., "In vitro engineered cartilage using synovium-derived mesenchymal stem cells with injectable gellan hydrogels." Acta biomaterialia 6.3 (2010): 1178-1185.*
Oliveira et al., Gellan gum injectable hydrogels for cartilage tissue engineering applications: in vitro studies and preliminary in vivo evaluation, 2009, Tissue Engineering Part A 16(1): 343-353.*
Sigma catalog product information for product G1910 (GELZAN™ CM), accessed Apr. 30, 2015 at: http://www.sigmaaldrich.com/catalog/product/sigma/g1910?lang=en&region=US.*

(Continued)

*Primary Examiner* — Robert J Yamasaki
(74) *Attorney, Agent, or Firm* — Leydig, Voit & Mayer, Ltd.

(57) ABSTRACT

The present invention relates to a protein production accelerating agent that has enabled to largely increase the produced amount of a desired protein by adding polysaccharides to a medium for animal cells containing a serum or serum alternative, and a production method of a protein using a medium containing the protein production accelerating agent.

18 Claims, 8 Drawing Sheets

(56) References Cited

FOREIGN PATENT DOCUMENTS

| | | |
|---|---|---|
| JP | 2006-204292 A | 8/2006 |
| JP | 2008-011797 A | 1/2008 |
| JP | 2008-061609 A | 3/2008 |
| JP | 2009-029967 A | 2/2009 |
| JP | 2009-050194 A | 3/2009 |
| JP | 2009-540826 A | 11/2009 |
| JP | 2010-512750 A | 4/2010 |
| JP | 2010-525836 A | 7/2010 |
| JP | 2011-024423 A | 2/2011 |
| JP | 2012-065555 A | 4/2012 |
| JP | 2012-105609 A | 6/2012 |
| JP | 2012-249547 A | 12/2012 |
| RU | 2267532 C1 | 1/2006 |
| WO | WO 2004/101774 A1 | 11/2004 |
| WO | WO 2005/028639 A2 | 3/2005 |
| WO | WO 2006/090886 A1 | 8/2006 |
| WO | WO 2008/002329 A2 | 1/2008 |
| WO | WO 2009/066468 A1 | 5/2009 |
| WO | WO 2009/137629 A2 | 11/2009 |
| WO | WO 2010/059775 A1 | 5/2010 |
| WO | WO 2010/079602 A1 | 7/2010 |
| WO | WO 2010/098079 A1 | 9/2010 |
| WO | WO 2011/002959 A1 | 1/2011 |
| WO | WO 2011/034604 A2 | 3/2011 |
| WO | WO 2003/046141 A1 | 6/2012 |
| WO | WO 2013/014472 A1 | 1/2013 |
| WO | WO 2013/017905 A1 | 2/2013 |
| WO | WO 2013/144372 A1 | 10/2013 |
| WO | WO 2014/017513 A1 | 1/2014 |
| WO | WO 2015/111685 A1 | 7/2015 |

OTHER PUBLICATIONS

Sigma catalog product information for ITS media additive, accessed Apr. 30, 2015 at: http://www.sigmaaldrich.com/catalog/product/sigma/i3146?lang=en&region=US.*
Product information for Dubelco's Modified Eagle Medium (DMEM), accessed online on Apr. 30, 2015 at: http://himedialabs.com/TD/AT149.pdf.*
Castro, Paula ML, et al. "Application of a statistical design to the optimization of culture medium for recombinant interferon-gamma production by Chinese hamster ovary cells." Applied microbiology and biotechnology 38.1 (1992): 84-90.*
Van Es, H. H., et al. "Expression of the plasmodial pfmdrl gene in mammalian cells is associated with increased susceptibility to chloroquine." Molecular and cellular biology 14.4 (1994): 2419-2428.*
Dreveton, Eric, et al. "Influence of fermentation hydrodynamics on gellan gum physico-chemical characteristics." Journal of fermentation and bioengineering 82.3 (1996): 272-276.*
Corning Microplate Selection Guide, 2007, accessed Sep. 7, 2017 at: http://www.level.com.tw/html/ezcatfiles/vipweb20/img/img/20297/productselectionguide_microplates11_02_cls_mp_014.pdf.*
Furue et al., *Proc. Natl. Acad. Sci.*, 105(36): 13409-13414 (2008).
Japanese Patent Office, International Search Report in International Patent Application No. PCT/JP2013/072500 (dated Oct. 1, 2013).
Bissell et al., *J. Clin. Investigation*, 79: 801-812 (Mar. 1987).
Brophy et al., *Hepatology*, 49: 578-586 (2009).
CP KELCO APS, "KELCOGEL® Gellan Gum Book," 5th ed. (2007) [available online at: http://www.appliedbioscience.com/docs/Gellan_Book_5th_Edition.pdf].
King et al., *Curr. Opin. Chem. Biol.*, 11(4): 394-398 (2007).
Klimanskaya et al., *Lancet*, 365: 1636-1641 (2005).
Lecluyse et al., *Critical Reviews in Toxiclology*, 42(6): 501-548 (2012).
Leung et al., *Tissue Engineering*, 17(2): 165-172 (2011).
Lin et al., *Biotechnology Journal*, 3: 1172-1184 (2008).
Liu et al., *Soft Matter*, 7: 5430-5436 (2011).
Mendes, Paula M., *Chem. Soc. Rev.*, 37: 2512-2529 (2008).
Moon et al., *Chem. Soc. Rev.*, 41: 4860-4883 (2012).
Murua et al., *Journal of Controlled Release*, 132: 76-83 (2008).

Nickerson et al., *Food Hydrocolloids*, 17(5): 577-583 (2003).
Pek et al., *Nature Nanotechnology*, 3: 671-675 (2008).
Sato et al., *Regenerative Medicine*, 4 (Suppl.): 96, abstract WS-5-5 (Feb. 10, 2005).
Stahl et al., *Biochemical and Biophysical Research Communications*, 322: 684-692 (2004).
Takamura et al., *Int. J. Cancer*, 98: 450-455 (2002).
Van Zijl et al., *World J. Hepatol.*, 2(1): 1-7 (2010).
Weathers et al., *Appl. Microbiol. Biotechnol.*, 85: 1339-1351 (2010).
Yang et al., *Proc. Natl. Acad. Sci. USA*, 76(7): 3401-3405 (1979).
Japanese Patent Office, International Search Report in International Patent Application No. PCT/JP2013/070001 (dated Oct. 15, 2013).
European Patent Office, Supplementary Partial European Search Report in European Patent Application No. 13831441 (dated Dec. 21, 2015).
Champagne et al., *Food Research International*, 29(5-6): 555-562 (1996).
Freyer et al., *Cytometry*, 10(6): 803-806 (1989).
Fujishige et al., *FEMS Microbiology Ecology*, 56: 195-206 (2006).
Huang et al., *International Journal of Food Science & Technology*, 39(10): 1009-1016 (2004).
Ichi et al., *Agric. Biol. Chem.*, 50(9): 2397-2399 (1986).
Otsuji et al., *Stem Cell Reports*, 2(5): 734-745 (2014).
Smith et al., *J. Biomater. Appl.*, 22(3): 241-254 (2007).
European Patent Office, Extended European Search Report in European Patent Application No. 13823078.4 (dated Feb. 16, 2016).
European Patent Office, Extended European Search Report in European Patent Application No. 13831441.4 (dated May 13, 2016).
Brenner, *Genetics*, 77(1): 71-94 (1974).
Fonkwe et al., *Food Hydrocolloids*, 17: 871-883 (2003).
Muschiol et al., *Nematology*, 9(2): 271-284 (2007).
New Energy and Industrial Technology Development Organization (NEDO), "Beyond the Fusion of Academia and Industry in Japan: An Integrated System for High Quality and Large Scale Production of hPSCs and Derivative Cells," Control No. 20140000000397, Project No. P10027 (Mar. 10, 2015) [downloaded from https://app5.infoc.nedo.go.jp/disclosure/SearchResultDetail on Nov. 15, 2016].
Wako Pure Chemical Industries, Ltd., "FCeM-series Preparation kit for ES/iPS Cells," printout from online catalog at siyaku.com (downloaded from www.siyaku.com on Nov. 14, 2016).
Wong et al., *Journal of Dairy Science*, 61(12): 1700-1703 (1978).
Chinese Patent Office, Second Office Action and Search Report in Chinese Patent Application No. 201380043529.5 (dated Jan. 22, 2017).
Ahearne et al., *Biomedical Materials*, 8(3): 035004 (2013).
Bodine et al., *Proc. Natl. Acad. Sci. USA*, 86(22): 8897-8901 (1989).
Coutinho et al., *Biomaterials*, 31(29): 7494-7502 (2010).
Dias et al., *Stem Cells and Development*, 20(9): 1639-1647 (2011).
Dolznig et al., *Curr. Biol.*, 12: 1076-1085 (2002).
Fujimi et al., *Int. J. Hematol.*, 87: 339-350 (2008).
Giarratana et al., *Blood*, 118(19): 5071-5079 (2011).
Hiroyama et al., *PLoS One*, 3(2): e1544 (2008).
Kishimoto et al., *Journal of Controlled Release*, 133: 185-190 (2009).
Ma et al., *Proc. Natl. Acad. Sci. USA*, 105: 13087-13092 (2008).
Mountford et al., *British Journal of Haematology*, 149: 22-34 (2010).
Otani et al., "Kobunshi Zairyo o Mochiita Xhinki Sanjigen Baiyoho no Kaihatsu," *The 36th Annual Meeting of the Molecular Biology Society of Japan*, Poster 2P-0990 (Nov. 20, 2013).
Watanabe et al., "The Biological Behavior of Prostate Cancer Cells in 3D Culture Systems" *Yakugaku Zasshi*, 128(1): 37-44 (2008).
European Patent Office, Extended European Search Report in European Patent Application No. 14785390.7 (dated Aug. 5, 2016).
Japanese Patent Office, Office Action in Japanese Patent Application No. 2014-177554 (dated Jun. 20, 2017).
Japanese Patent Office, International Search Report in International Patent Application No. PCT/JP2014/060829 (dated Jul. 1, 2014).
Japanese Patent Office, Written Opinion of the International Searching Authority in International Patent Application No. PCT/JP2014/060829 (dated Jul. 1, 2014).

(56) References Cited

OTHER PUBLICATIONS

Deasy et al., "Rheological evaluation of deacetylated gellan gum (Gelrite) for pharmaceutical use," *International Journal of Pharmaceutics*, 73(2): 117-123 (1991).
Chinese Patent Office, The Fourth Office Action in Chinese Patent Application No. 201380043529.5 (dated Nov. 27, 2017).
Rule et al., "Gellan Gum as a Substitute for Agar in Leptospiral Media," *J. Clin. Microbiol.*, 23(3): 500-504 (1986).
Russian Patent Office, Official Action in Russian Patent Application No. 2015106003 (dated Jun. 14, 2017).
U.S. Appl. No. 13/949,310, filed Jul. 24, 2013.
U.S. Appl. No. 14/784,843, filed Oct. 15, 2015.
U.S. Appl. No. 15/448,557, filed Mar. 2, 2017.

* cited by examiner

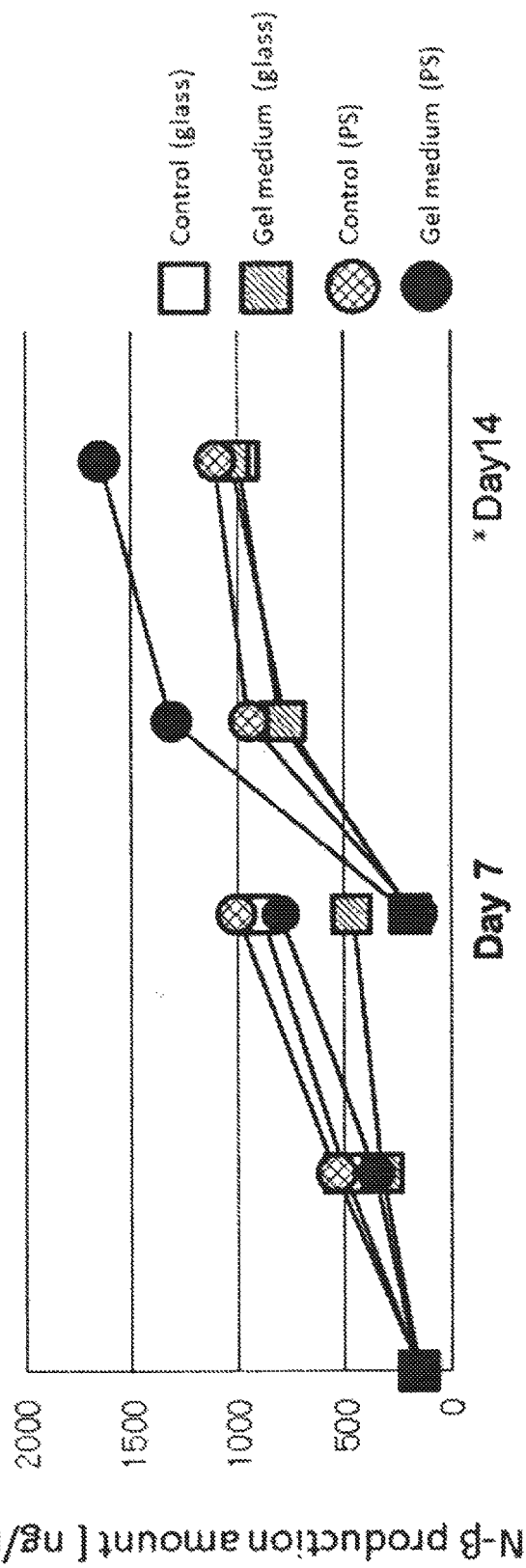

ENHANCING INGREDIENTS FOR PROTEIN PRODUCTION FROM VARIOUS CELLS

CROSS-REFERENCE TO RELATED APPLICATIONS

This patent application claims the benefit of U.S. Provisional Patent Application No. 61/692,549 filed on Aug. 23, 2012, which is incorporated by reference in its entirety herein.

INCORPORATION-BY-REFERENCE OF MATERIAL ELECTRONICALLY SUBMITTED

Incorporated by reference in its entirety herein is a computer-readable nucleotide/amino acid sequence listing submitted on Aug. 23, 2013 and identified as follows: 678 bytes ASCII (Text) file named "714151SequenceListing.txt," created Aug. 23, 2013.

TECHNICAL FIELD

The present invention relates to cell culture, particularly, to a protein production accelerating agent suitable for high production of protein by an animal cell (for example, CHO cell) and a medium containing the same. Moreover, the present invention relates to a production method of protein using the protein production accelerating agent and a medium containing the same.

BACKGROUND ART

In recent years, in the field of life sciences, it is becoming highly important to produce an object useful protein in an industrial scale by mass culture of an animal cell that produces the useful protein. When a natural or recombinant protein and the like are produced by culturing the animal cell or an animal cell introduced with a gene encoding a desired protein, an animal cell growth factor is used besides the basic nutrients, such as salts, saccharides, amino acids, vitamins and the like, for the growth of the animal cell. As the animal cell growth factor, serum components such as fetal bovine serum, calf serum and the like are generally used. In general, when fetal bovine serum or calf serum is used, it needs to be added to a basal medium in about 5-20 volume %.

However, sera such as fetal bovine serum, calf serum and the like are in limited supply and are generally highly expensive. This leads to an increased production cost of the useful protein.

Moreover, mammal-derived growth factors and sera are problematic since they are related to mad cow disease, Bovine Spongiform Encephalopathy, transmissible spongiform encephalopathy, and further, prion-related diseases such as Creutzfeldt-Jakob disease, and mammal-derived serum may be contaminated with virus or mycoplasma since it cannot be sterilized in autoclave and the like. From the aspect of safety, therefore, a serum-free culture method has been developed wherein animal cells are cultivated in the absence of serum. In the serum-free culture method, naturally occurring purified proteins such as insulin, transferrin, growth factor and the like, recombinant proteins and the like are used as a substance that substitutes the effect of serum (serum alternative). However, these proteins are generally more expensive than fetal bovine serum or calf serum, and the supply thereof is limited.

As mentioned above, since serum and serum alternatives are expensive, and the supply thereof is limited, the development of a technique for producing useful proteins still more efficiently is desired.

SUMMARY OF THE INVENTION

Problems to be Solved by the Invention

The problem of the present invention is provision of a protein production accelerating agent for producing a desired protein by using an animal cell. A further problem of the present invention is provision of a production method of a protein by using a medium containing the protein production accelerating agent.

Means of Solving the Problems

The present inventors have conducted intensive studies in an attempt to solve the aforementioned problems and found that addition of a polysaccharide to a medium for animal cells containing a serum or serum alternative markedly increases the amount of a desired protein produced, which resulted in the completion of the present invention.

Accordingly, the present invention relates to the following [1]-[15].

[1] A medium additive for animal cell, comprising a polysaccharide.
[2] The additive of [1], which promotes production of a desired protein by an animal cell to be cultivated.
[3] The additive of [2], which promotes production of a protein per 1 cell of the aforementioned animal cell.
[4] The additive of [1], wherein the aforementioned polysaccharide has an anionic functional group.
[5] The additive of [4], wherein the aforementioned anionic functional group is at least one kind selected from the group consisting of a carboxy group, a sulfo group and a phosphate group.
[6] The additive of [5], wherein the aforementioned polysaccharide is at least one kind selected from the group consisting of hyaluronic acid, gellan gum, deacylated gellan gum, xanthan gum, carageenan, diutan gum, alginic acid, fucoidan, pectin, pectic acid, pectinic acid, heparan sulfate, heparin, heparitin sulfate, keratosulfate, chondroitin sulfate, dermatan sulfate, rhamnan sulfate and salts thereof.
[7] The additive of [6], wherein the aforementioned polysaccharide is deacylated gellan gum or a salt thereof.
[8] A medium for animal cell, comprising the additive of any one of [1] to [7].
[9] The medium of [8], having a serum concentration of not less than 1% (w/v) and not more than 15% (w/v).
[10] The medium of [8], having a serum alternative concentration of not less than 1% (w/v) and not more than 15% (w/v), wherein the serum alternative is selected from the group consisting of a plasma protein, a hormone, a growth factor and a salt.
[11] The medium of any one of [8] to [10], further comprising at least one kind selected from the group consisting of amino acids, vitamins, energy sources, osmoregulators, iron sources and pH buffers.
[12] A method of producing a protein by using an animal cell culture, comprising cultivating the animal cell in the presence of the additive of any one of [1] to [7] or in the medium of any one of [8] to [11].
[13] The method of [12], wherein the animal cell is cultivated for at least period (a) or (b):

(a) a part or all of the period when the animal cell to be cultivated can sufficiently grow,
(b) a part or all of the period when the animal cell can sufficiently produce a desired protein.
[14] A method of promoting the amount of a protein produced by an animal cell in a culture medium, comprising cultivating the animal cell in the presence of the additive of any one of [1] to [7] or in the medium of any one of [8] to [11].
[15] The method of [14], which promotes the amount of the produced protein per 1 cell of the animal cell.

Effect of the Invention

The medium additive for animal cell of the present invention can increase the produced amount of a desired protein, when it is added to a culture medium for animal cell, an animal cell capable of producing the protein is cultured using the obtained medium, and the produced protein is collected from the medium and/or the animal cell. Particularly, it can increase the amount of the produced protein per 1 cell.

In addition, since the medium additive for animal cell of the present invention can promote the produced amount of a desired protein by simple addition to the medium, it is advantageous from the aspects of operation and handling.

Furthermore, since the additive can produce a desired protein more efficiently, it is also advantageous from the aspect of production cost, and can greatly contribute to, for example, mass supply of biopharmaceutical products such as an antibody drug and the like, and the like.

BRIEF DESCRIPTION OF THE DRAWINGS

FIG. 8 shows an influence of the difference in the material of a roller bottle on IFN-β production of cells in gel.

DESCRIPTION OF EMBODIMENTS

1. Medium Additive/Protein Production Accelerating Agent

Figure 1:
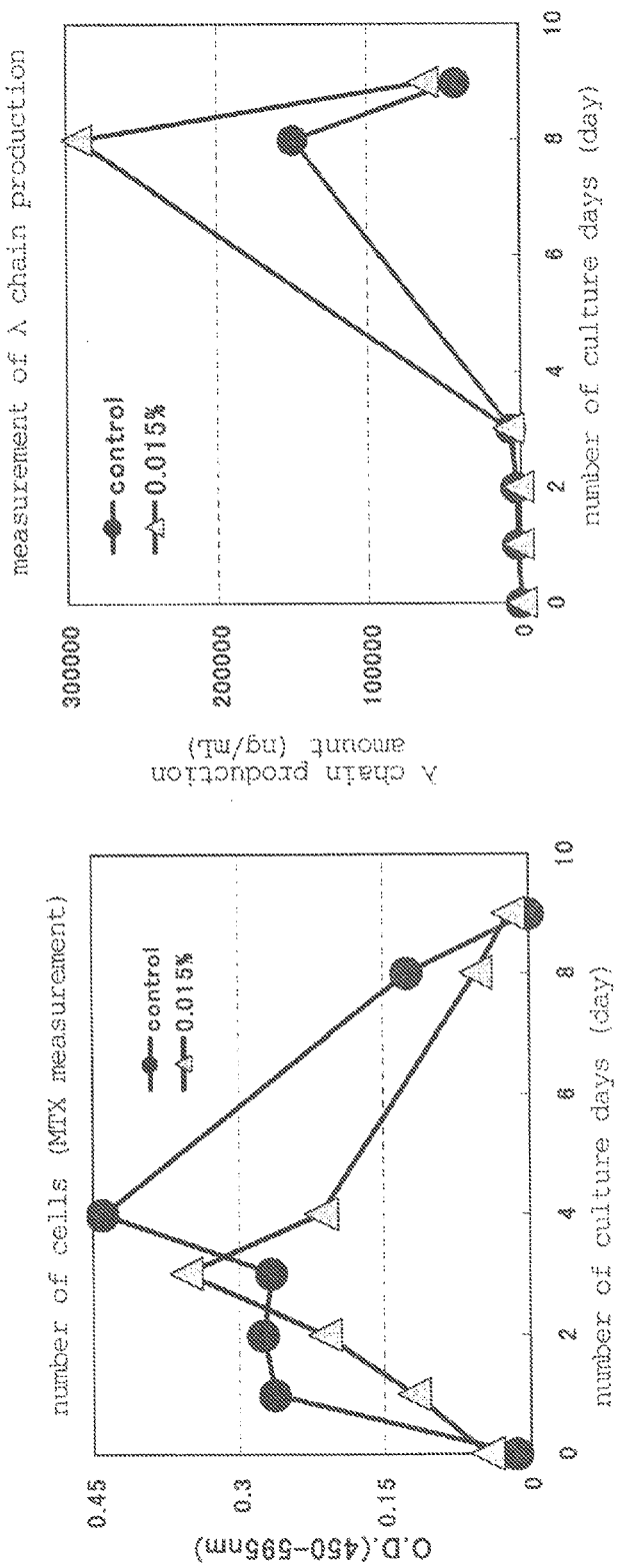
FIG. 1 shows comparison of cell number increase and λ chain production amount when human myeloma derived cell line SC-01MFP was cultured in the presence of deacylated gellan gum (0.015%) and in the absence thereof (control).

The present invention is based on the finding that, when a protein is produced using an animal cell, the object protein can be highly produced at least partially by adding polysaccharide to a culture medium at least for a period when the cell to be cultivated can sufficiently grow or a part or all of a period when the desired protein to be produced can be sufficiently produced. Therefore, the present invention provides a medium additive for animal cell containing the polysaccharide, an agent for accelerating protein production by the animal cell (hereinafter sometimes to be abbreviated as "the medium additive/protein production accelerating agent of the present invention").

The polysaccharides to be used in the present invention preferably have an anionic functional group. As the anionic functional group, a carboxyl group, a sulfo group, a phosphate group and salts thereof can be mentioned, and a carboxyl group or a salt thereof is preferable.

The polysaccharides to be used in the present invention, wherein not less than 10 monosaccharides (e.g., triose, tetrose, pentose, hexsauce, heptose etc.) are polymerized, more preferably, acidic polysaccharides having an anionic functional group. The acidic polysaccharides here is not particularly limited as long as it has an anionic functional group in the structure thereof, and includes, for example, polysaccharides having a uronic acid (e.g., glucuronic acid, iduronic acid, galacturonic acid, mannuronic acid), polysaccharides having a sulfuric acid group or phosphate group in a part of the structure thereof, and polysaccharides having the both structures, and includes not only naturally-obtained polysaccharides but also polysaccharides produced by microorganisms, polysaccharides produced by genetic engineering, and polysaccharides artificially synthesized using an enzyme. More specifically, examples thereof include polymer compounds composed of one or more kinds selected from the group consisting of hyaluronic acid, gellan gum, deacylated gellan gum, rhamsan gum, diutan gum, xanthan gum, carageenan, xanthan gum, hexuronic acid, fucoidan, pectin, pectic acid, pectinic acid, heparan sulfate, heparin, heparitin sulfate, keratosulfate, chondroitin sulfate, dermatan sulfate, rhamnan sulfate and a salt thereof.

The salt here includes, for example, alkali metal salts such as lithium, sodium, potassium, salts with alkaline earth metals such as calcium, barium, magnesium and salts with aluminum, zinc, copper, iron, ammonium, organic base and amino acid and the like salt. Preferable examples thereof include, but are not limited to, divalent metal salts such as calcium, magnesium, zinc, iron, copper and the like.

The weight average molecular weight of these is preferably 10,000 to 50,000,000, more preferably 100,000 to 20,000,000, more preferably 1,000,000 to 10,000,000. The molecular weight in the present invention, can be measured based on pullulan by gel penetration chromatography (GPC).

More preferable specific examples of the polysaccharides to be used in the present invention include deacylated gellan gum, carageenan and xanthan gum, most preferably example includes deacylated gellan. The deacylated gellan gum in the present invention is a linear polymer polysaccharide containing 4 molecules of sugars of 1-3 bonded glucose, 1-4 bonded glucuronic acid, 1-4 bonded glucose and 1-4 bonded rhamnose as the constituent unit, which is a polysaccharide of the following formula (I) wherein R1, R2 are each a hydrogen atom, and n is an integer of two or more. R1 may contain a glyceryl group, R2 may contain an acetyl group, and the content of the acetyl group and glyceryl group is preferably not more than 10%, more preferably not more than 1%.

trade mark of CP Kelco)" manufactured by San-Ei Gen F.F.I., Inc. and the like can be used.

The medium additive/protein production accelerating agent in present invention can contain, in addition to any of the above-mentioned polysaccharides, various components generally added to a medium additive. Alternatively, the polysaccharide itself may be singly used as the medium additive/protein production accelerating agent of the present invention.

The medium additive of the present invention can be appropriately added to the medium within the range free of an unpreferable influence on the culture of the animal cell, as long as it can exhibit a function as a protein production accelerating agent, that is, as long as it significantly increases the production amount of the object protein to be produced by the animal cell, compared to that without addition of the polysaccharide. For example, the medium

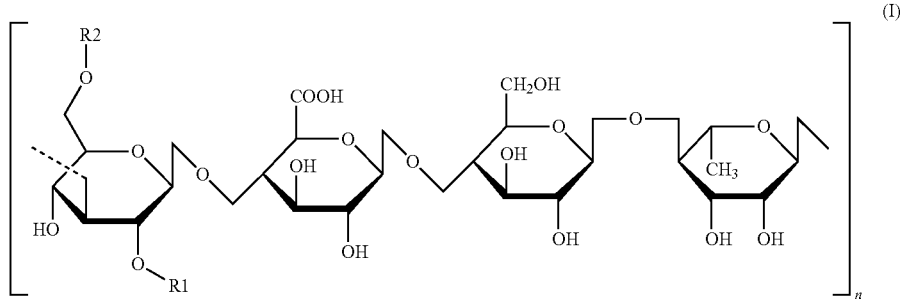

(I)

The polysaccharides in the present invention can be obtained by a chemical synthesis method. When the compound is a naturally-occurring substance, it is preferably obtained from various plants, various animals, various microorganisms containing the compound by extraction, separation and purification by conventional techniques. For extraction, the compound can be extracted efficiently by using water and supercritical gas. For example, as a production method of gellan gum, a gellan gum producing microorganism is cultured in a fermentation medium, a mucosal substance produced outside fungus is recovered by a general purification method and, after the steps of drying, pulverizing and the like, powderized. When it is deacylated gellan gum, an alkali treatment is applied when an aforementioned mucous substance is recovered, the glyceryl group and the acetyl group bonded to 1-3 bonded glucose residue are deacylated and recovered. Examples of the purification method include liquid-liquid extraction, fractional precipitation, crystallization, various kinds of ion exchange chromatography, gel filtration chromatography using Sephadex LH-20 and the like, adsorption chromatography using activated carbon, silica gel and the like, adsorption and desorption treatment of active substance by thin layer chromatography, high performance liquid chromatography using reversed-phase column and the like, and impurity can be removed and the compound can be purified by using them singly or in combination in any order, or repeatedly. Examples of the gellan gum-producing microorganism include, but are not limited to, *Sphingomonas elodea* and microorganism obtained by altering the gene of *Sphingomonas elodea*. Furthermore, when it is deacylated gellan gum, commercially available products, for example, "KELCOGEL (registered trade mark of CP Kelco) CG-LA" manufactured by SANSHO Co., Ltd., "KELCOGEL (registered additive of the present invention medium only needs to be added such that the concentration of the above-mentioned polysaccharide in the medium is 0.001% to 1.0% (weight/volume, hereinafter sometimes to be abbreviated as w/v), preferably 0.002% to 0.4% (weight/volume), more preferably 0.005% to 0.2% (weight/volume), still more preferably 0.005% to 0.05% (weight/volume). For example, when deacylated gellan gum is used as the polysaccharide, it is added to a medium at 0.001% to 1.0% (weight/volume), preferably 0.001% to 0.5% (weight/volume), more preferably 0.005% to 0.1% (weight/volume), most preferably, 0.01% to 0.05% (weight/volume). The concentration can be calculated by the following formula.

Concentration (%)=weight (g) of particular compound/volume (ml) of medium composition×100

2. Medium Composition

The medium for which the medium additive of the present invention can be used is not particularly limited as long as it is a medium for animal cells. According to the classification by the composition of the medium, for example, natural medium, semisynthetic medium and synthetic medium can be mentioned. According to the classification by the shape, semi-solid medium, liquid medium and the like can be mentioned. Examples thereof include, but are not limited to, Dulbecco's modified Eagle medium (DMEM), hamF12 medium (Ham's Nutrient Mixture F12), DMEM/F12 medium, McCoy's 5A medium, Eagle MEM medium (Eagles's Minimum Essential Medium; EMEM), αMEM medium (alpha Modified Eagles's Minimum Essential Medium; αMEM), MEM medium (Minimum Essential Medium), RPMI 1640 medium, Iscove's Modified Dulbecco's medium (IMDM), MCDB131 medium, William medium E, IPL41 medium, Fischer's medium, E-RDF medium (manufactured by KYOKUTO PHARMACEUTICAL INDUSTRIAL CO., LTD.), Ultra CHO (registered trade mark) medium (manufactured by Lonza), EX-CELL (registered trade mark) 302 medium (manufactured by Sigma Aldrich), EX-CELL (registered trade mark) 325-PF medium (manufactured by Sigma Aldrich), EX-CELL (registered trade mark) ACF CHO medium (manufactured by Sigma Aldrich), EX-CELL (registered trade mark) CHO DHFR medium (manufactured by Sigma Aldrich), EX-CELL (registered trade mark) CD CHO medium (manufactured by Sigma Aldrich), EX-CELL (registered trade mark) CD CHO-2 medium (manufactured by Sigma Aldrich), EX-CELL (registered trade mark) CD CHO-3 medium (manufactured by Sigma Aldrich), CD OptiCHO (registered trade mark) medium (manufactured by Life Technologies), CD CHO medium (manufactured by Life Technologies), CD CHO AGT (registered trade mark) medium (manufactured by Life Technologies), CD FortiCHO (registered trade mark) medium (manufactured by Life Technologies), CHO-S-SFMII medium (manufactured by Life Technologies), CD DG44 medium (manufactured by Life Technologies), HyClone CDM4-CHO medium (manufactured by Thermo Scientific), HyClone SFM4-CHO medium (manufactured by Thermo Scientific), CD-ACP-CHO (manufactured by Sigma Aldrich), HyClone SFM4-CHO-Utillity medium (manufactured by Thermo Scientific), KBM270 medium (manufactured by Kohjin Bio Co., Ltd.), KBM240 medium (manufactured by Kohjin Bio Co., Ltd.), KBM230 medium (manufactured by Kohjin Bio Co., Ltd.), KBM306 medium (manufactured by Kohjin Bio Co., Ltd.), BD Select CHO medium (manufactured by Becton, Dickinson and Company), CHOMACS CD medium (manufactured by Miltenyi Biotec), ESF SFM medium (manufactured by Expression Systems), Daigo's T medium (manufactured by NIHON PHARMACEUTICAL CO., LTD.), IS CHO-V medium (registered trade mark) (Irvin Scientific), IS CHO-V-GS medium (registered trade mark) (Irvin Scientific), Opti-Pro (manufactured by Invitrogen) and the like.

Those of ordinary skill in the art can add, to the above-mentioned medium, one kind from various amino acids, various vitamins, energy sources, osmoregulators, iron sources, pH buffers, antibiotics and the like, or two or more thereof in combination. Furthermore, those of ordinary skill in the art can also add one or more kinds of other chemical components or biological components in combination according to the object.

As various amino acids, L-alanine, L-arginine, L-asparagine, L-aspartic acid, L-cysteine, L-cystine, L-glutamine, L-glutamic acid, glycine, L-histidine, L-isoleucine, L-leucine, L-lysine, L-methionine, L-ornithine, L-phenylalanine, L-proline, L-serine, L-threonine, L-tryptophan, L-tyrosine, L-valine and the like can be used, as various vitamins, biotin, folic acid, lipoic acid, nicotineamide, nicotinic acid, p-aminobenzoic acid, panthothenic acid calcium salt, pyridoxal hydrochloride, pyridoxine hydrochloride, riboflavin, thiamine hydrochloride, vitamin B12, ascorbic acid and the like can be used, as energy source, glucose, galactose, mannose, fructose and the like can be used, as osmotic pressure regulator, sodium chloride, potassium chloride, potassium nitrate and the like can be used, as iron source, Fe-EDTA, ferric citrate, ferrous chloride, ferric chloride, ferrous sulfate, ferric sulfate, ferric nitrate and the like can be used and, as pH buffering agent, sodium hydrogen carbonate, calcium chloride, sodium dihydrogen phosphate, HEPES, MOPS and the like can be used. Those of ordinary skill in the art can appropriately adjust the concentration of addition according to the kind of the cell to be cultivated and the like.

Examples of the antibiotic to be added to a medium include, but are not limited to, Sulfonamides and preparations, penicillin, phenethicillin, methicillin, oxacillin, cloxacillin, dicloxacillin, flucloxacillin, nafcillin, ampicillin, penicillin, amoxicillin, ciclacillin, carbenicillin, ticarcillin, piperacillin, azlocillin, mezlocillin, mecillinam, andinocillin, cephalosporin and a derivative thereof, oxolinic acid, amifloxacin, temafloxacin, nalidixic acid, Piromidic acid, ciprofloxacin, cinoxacin, norfloxacin, perfloxacin, Rosaxacin, ofloxacin, enoxacin, pipemidic acid, sulbactam, clavulanic acid, β-bromopenisillanic acid, β-chloropenisillanic acid, 6-acetylmethylene-penisillanic acid, cephoxazole, sultampicillin, adinoshirin and, tazobactam, aztreonam, sulfazethin, isosulfazethin, norcardicin, m-carboxyphenyl, phenylacetamidophosphonic acid methyl, Chlortetracycline, oxytetracycline, tetracycline, demeclocycline, doxycycline, methacycline, and minocycline. Those of ordinary skill in the art can appropriately adjust the concentration of addition according to the kind of the cell to be cultivated and the like.

When the medium additive of the present invention is added to the above-mentioned medium, a medium additive is dissolved in an appropriate solvent when in use, and the additive solution is added to the medium such that the concentration of polysaccharides in the medium falls within the above-mentioned range. Here, examples of the appropriate solvent include, but are not limited to, water, dimethyl sulfoxide (DMSO), various alcohols (e.g., methanol, ethanol, butanol, propanol, glycerol, propylene glycol, butyleneglycol and the like) and the like.

In a preparation method of the above-mentioned medium additive solution, a medium additive is first added to the above-mentioned solvent, and dissolved by heating while stirring at a temperature capable of dissolving polysaccharides (e.g., 60° C., 80° C., 90° C. or above). After dissolution, the mixture is allowed to cool with stirring, sterilized (e.g., autoclave sterilization at 121° C. for 20 min), and cooled to room temperature. The solution after the aforementioned sterilization is added to a medium, and the mixture is uniformly mixed. For example, when deacylated gellan gum is prepared, deacylated gellan gum is added to ion exchange water or ultrapure water to 0.1% to 2.0% (weight/volume), 0.2% to 1.0% (weight/volume), preferably 0.2% to 0.5% (weight/volume), more preferably 0.2% to 0.4% (weight/volume). Then, the mixture is stirred with heating to any temperature at which the aforementioned deacylated gellan gum can be dissolved, which is not less than 60° C., preferably not less than 80° C., more preferably not less than 90° C., to allow for dissolution to a transparent state. After dissolution, the mixture is allowed to cool with stirring, and sterilized (for example, autoclave at 121° C. for 20 min), after cooling to room temperature, the aqueous solution is added to a medium and the mixture is uniformly mixed. The mixing method is not particularly limited and, for example, may be manual mixing such as pipetting etc., or mixing with an instrument such as magnetic stirrer, mechanical stirrer, homomixer and homogenizer. Furthermore, the medium mixture can be filtrated through a filter after mixing.

The deacylated gellan gum prepared as mentioned above and in a gel state can be micronized and used for cell culture. The micronization means is, for example, a physicochemical method. For example, a chemical means using EDTA, potassium oxalate and the like, and a physical means using UV, ultrasonication and the like, which are described in the below-mentioned Examples, can be mentioned. The gel micronized by these means can be used by resuspending when added to a culture medium.

The concentrations of the serum and serum alternative in the medium composition for animal cell of the present invention, which contains the medium additive/protein production accelerating agent of the present invention and prepared as mentioned above, are shown.

For example, in the case of serum, a serum-free medium or a serum medium having a serum concentration of 1%-15% (weight/volume), 1%-10% (weight/volume), 5%-15% (weight/volume), 5%-10% (weight/volume) can be mentioned. In the case of serum alternative, a medium free of the alternative or a medium containing the alternative at a concentration, at which the function of the serum in the aforementioned concentration range is substituted (e.g., 1%-15% (weight/volume), 1%-10% (weight/volume), 5%-15% (weight/volume), 5%-10% (weight/volume)), can be mentioned.

3. Cell Culture Method

In the present invention, any culture method from batch culture method, continuous culture method, and fed-batch culture method, which are general cell culture methods, may be used. Preferably, fed-batch culture method or continuous culture method is used, particularly preferably, fed-batch culture method is used.

The batch culture method is a culture method wherein a small amount of a seed culture medium is added to a medium and cells are grown without newly adding a medium or discharging the culture medium during culture. When the batch culture method is used in the present invention, a culture medium containing the medium additive of the present invention can be used as a seed culture medium.

The continuous culture method is a culture method wherein a culture medium is continuously added and continuously discharged during the culture. The continuous method also includes perfusion culture.

The fed-batch culture method is also called a semi-batch culture method since it is in between the batch culture method and the continuous culture method, wherein a medium is added continuously or sequentially during culture, but the medium is not discharged continuously unlike the continuous culture method. The medium to be added during fed-batch culture (hereinafter fed-batch medium) does not need to be the same as the culture medium already used for the culture (hereinafter initial culture medium), and a different culture medium may be added or a particular component alone may be added.

In the present invention, the initial culture medium refers to a culture medium generally used in the initial stage of cell culture. However, when a fed-batch culture medium is added in plural portions, a culture medium before addition of the fed-batch culture medium may be used as the initial culture medium. Cells can be cultivated using a culture medium containing the above-mentioned medium additive of the present invention as the initial culture medium. The concentration of polysaccharides to be added to the initial culture medium only needs to be a concentration capable of increasing the amount of the produced object protein. For example, polysaccharides are added to the culture medium to afford 0.001% to 1.0% (weight/volume), preferably 0.002% to 0.4% (weight/volume), more preferably 0.005% to 0.2% (weight/volume), still more preferably 0.005% to 0.05% (weight/volume).

In the present invention, when the fed-batch culture method or continuous culture method is used, a culture medium containing the above-mentioned medium additive of the present invention can be used as a culture medium to be added during culture. The culture medium to be added in the fed-batch culture (fed-batch culture medium) is desirably a high concentration medium to prevent an increase in the culture volume. Specifically, for example, a fed-batch medium having a polysaccharide concentration of 0.001% to 1.0% (weight/volume), preferably 0.002% to 0.4% (weight/volume), more preferably 0.005% to 0.2% (weight/volume), still more preferably 0.005% to 0.05% (weight/volume), can be used as a fed-batch culture medium.

In the present invention, when the aforementioned fed-batch culture medium is added to a culture medium, 1%-150%, preferably 5%-50%, more preferably 8%-20%, of the initial culture medium volume can be used as a fed-batch culture medium volume to be added continuously, or for a given period, or sequentially throughout the culture period.

The culture method of the present invention is not particularly limited and can be used for culture of various animal cells. For example, it can cultivate a malignantly-transformed human cell, fusion cell represented by antibody-producing hybridoma such as mouse-human, mouse-mouse, mouse-rat and the like or COS cell or CHO cell incorporating, by a genetic engineering operation, a gene encoding a desired protein.

For example, SC-01MFP (cell line deposited in independent administrative corporation the National Institute of Advanced Industrial Science and Technology, FERM BP-10077) described in the below-mentioned Examples is cultured (WO2005/083060), whereby a native type protein naturally produced by the animal cell can be obtained. In addition, the method can also be utilized for cultivating a cell line highly producing a desired protein, which is obtained by transfection with an expression vector containing a nucleic acid encoding said protein.

In the present invention, a particularly preferable animal cell is a CHO cell introduced with a gene encoding a desired protein. Examples of CHO include, but are not limited to, CHO-K1 cell (ATCC CCL-61 (trademark)), CHO-S cell, DG44 cell and the like. The desired protein is not particularly limited, and may be any protein containing an antibody such as natural antibody, antibody fragment, low molecule weight antibody, chimeric antibody, humanized antibody, human antibody and the like (e.g., anti-IL-6 receptor antibody, anti-Glypican-3 antibody, anti-CD3 antibody, anti-$CD_2O$ antibody, anti-GPIIb/IIIa antibody, anti-TNF antibody, anti-CD25 antibody, anti-EGFR antibody, Her2/neu antibody, anti-RSV antibody, anti-CD33 antibody, anti-CD52 antibody, anti-IgE antibody, anti-CD11a antibody, anti-VEGF antibody, anti-VLA4 antibody and the like) and a physiologically active protein (granulocyte colony stimulating factor (GCSF), granulocyte macrophage colony stimulating agent (GM-CSF), erythropoietin, interferon, IL-1 and IL-6 and the like, interleukin, t-PA, urokinase, serum albumin, blood coagulation factor, and the like), and cytokines. Particularly, an immunity related protein containing an antibody or cytokine usable as a pharmaceutical product, a protein relating to cell proliferation differentiation, a membrane protein and the like are preferable.

Since the culture conditions vary depending on the kind of the cell to be used, it is possible to appropriately determine preferable conditions. Generally, for example, the culture conditions for CHO cell may be gaseous phase atmosphere of $CO_2$ concentration 0%-40%, preferably 2%-10%, culture medium pH of 6.5-7.2, preferably 6.7-7.0, more preferably 6.8-6.9, at 30° C.-39° C., preferably about 37° C., for 1 day-50 days, more preferably 1 day-14 days.

Examples of the various culture apparatuses for animal cell culture include, but are not limited to, fermentation vessel type tank culture apparatus, air lift type culture apparatus, culture flask type culture apparatus, spinner flask type culture apparatus, microcarrier type culture apparatus, fluidized bed type culture apparatus, hollow fiber type culture apparatus, roller bottle type culture apparatus, fill vessel type culture apparatus, bioreactor type culture apparatus and the like.

When cells are cultivated by the culture method of the present invention, culture tools generally used for cell culture such as schale, flask, plastic bag, Teflon (registered trade mark) bag, dish, petri dish, dish for tissue culture, multidish, microplate, microwell plate, multiplate, multiwall plate, chamber slide, cell culture flask, spinner flask, tube, tray, culture bag, roller bottle and the like can be used for cultivation.

The materials of these culture tools are, for example, glass, plastics such as polyvinyl chloride, cellulosic polymers such as ethylcellulose, acetylcellulose and the like, polystyrene, polymethylmethacrylate, polycarbonate, polysulfone, polyurethane, polyester, polyamide, polystyrene, polypropylene, polyethylene, polybutadiene, poly(ethylene-vinylacetate) copolymer, poly(butadiene-styrene)copolymer, poly(butadiene-acrylonitrile) copolymer, poly(ethylene-ethylacrylate) copolymer, poly(ethylene-methacrylate) copolymer, polychloroprene, styrol resin, chlorosulfonated polyethylene, ethylenevinyl acetate, acrylic block copolymer, and the like can be mentioned. As described in the below-mentioned Examples, since the roller bottle tools affect cell proliferation and the like in the gel in the present invention, polystyrene is preferable.

4. Production Method of Protein

By cultivating animal cells by the aforementioned cell culture method, a protein can be highly produced.

In general, production of a protein by an animal cell may require simple cultivation thereof or a special operation. The operation, conditions and the like therefor can be appropriately determined according to the animal cell to be cultivated. While the kind of the protein is not limited, in the case of, for example, CHO cell transformed with a vector containing a gene encoding a mouse-human chimeric antibody by a genetic engineering operation, culture under the aforementioned conditions affords a desired protein in the medium in 1 day-50 days, preferably 5 days-21 days, more preferably about 7 days-14 days. By isolation and purification according to a conventional method (see, for example, Introduction to antibody engineering, Chijinshokan, (1994), p. 102-104; Affinity Chromatography Principles & Methods, GE Healthcare, (2003), p. 56-60 and the like), the desired protein can be obtained.

According to the present invention, a recombinant antibody (natural antibody, antibody fragment, low molecular weight antibody, chimeric antibody, humanized antibody, human antibody, bispecific antibody and the like), a gene recombinant protein (granulocyte colony stimulating factor (G-CSF), granulocyte macrophage colony stimulating agent (GM-CSF), erythropoietin, interferon, interleukins such as IL-1 and IL-6 and the like, t-PA, urokinase, serum albumin, blood coagulation factor etc.), and the like can be produced in a high production amount.

The antibody to be produced by the production method of the present invention includes not only a monoclonal antibody derived from an animal such as human, mouse, rat, hamster, rabbit, monkey and the like, but also an artificially-altered gene recombinant antibody such as chimeric antibody, humanized antibody, human antibody, bispecific antibody and the like. In addition, the immune globulin class of the antibody is not particularly limited, and may be any class such as IgG (e.g., IgG1, IgG2, IgG3, IgG4 and the like), IgA, IgD, IgE, IgM and the like. When used as a medicament, IgG and IgM are preferable. Moreover, the antibody of the present invention includes not only whole antibody but also antibody fragments such as Fv, Fab, F(ab)$_2$ and the like, a low molecular weight antibody such as monovalent or divalent or more single strand Fv (scFv, sc(Fv)$_2$ etc.) wherein a variable region of the antibody is linked with a linker such as a peptide linker and the like, and the like.

The present invention is explained concretely in the following by way of Examples and Reference Examples. These Examples and the like are intended to explain the present invention, and do not limit the scope of the present invention.

Example 1

Sample

The cell line used in this Example is human myeloma-derived cell line SC-01MFP showing a characteristic production ability of antibody λ light chain protein (WO 2005/083060).

[Culture Evaluation System Using Deacylated Gellan Gum-Containing Medium]

Deacylated gellan gum powder (KELCOGEL CG-LA, manufactured by SANSHO Co., Ltd.) was dissolved in ultrapure water (Milli-Q water) at 3 g/L. The solution was warmed in hot water and, after confirmation of dissolution of deacylated gellan gum powder, sterilized by autoclave. The sterilized solution was stood still and allowed to cool to room temperature, and a mixed medium containing deacylated gellan gum at a concentration of 0.015% (w/v, hereinafter the same for deacylated gellan gum concentration) relative to 10% fetal bovine serum-containing E-RDF medium (manufactured by KYOKUTO PHARMACEUTICAL INDUSTRIAL CO., LTD.) was prepared. For a control group, 10% fetal bovine serum-containing E-RDF medium (manufactured by KYOKUTO PHARMACEUTICAL INDUSTRIAL CO., LTD.) without deacylated gellan gum was used. Then, the cells were plated on a 96 well immunoplate by 100 μL to 1×10$^4$ cells/well in the prepared deacylated gellan gum-containing medium. Every 24 hr, Cell Counting Kit8 (manufactured by DOJINDO LABORATORIES) was added at 10 μL/well and the mixture was incubated for 1.5 hr. The culture medium (100 μL) was transferred to another 96 well plate, and the absorbance was measured at 450-595 nm. As a result, as shown in FIG. 1, left, as compared to deacylated gellan gum no addition (control group), SC-01MFP cells did not show a remarkable difference from day 2 after the start of the culture and thereafter, in the increase in the cell number by culture in the 0.015% deacylated gellan gum-added medium.

[Measurement of Amount of Produced λ Chain by Enzyme Antibody Method]

Figure 2:
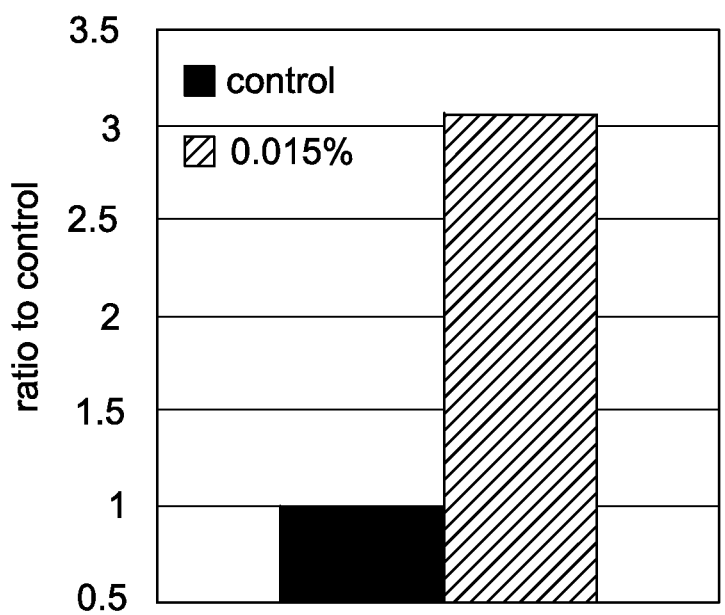
FIG. 2 shows comparison of λ chain production amount area under graph in the presence of deacylated gellan gum (0.015%) and that of control as 1, wherein the λ chain production amount area under graph was amended using the cell number increase area under graph obtained by calculating, by a trapezoid method, the area under graph of the cell number increase (left figure) and λ chain production amount (right figure) when SC-01MFP was cultured in the presence of deacylated gellan gum (0.015%) and in the absence thereof (control), in the test using SC-01MFP described in FIG. 1, (λ chain production amount area under graph/cell number increase area under graph).

The amount of λ chain produced in the above-mentioned culture supernatant was measured by an enzyme antibody method (ELISA; enzyme-linked immunosorbent assay). Goat anti-human λ chain antibody (BIOSORCE) was diluted 2000-fold with phosphate buffered saline (PBS) and dispensed to a 96 well immunoplate at 100 μL/well to coat the plate. After standing at 37° C. for 1 hr, to a solution obtained by diluting bovine serum albumin (BSA; ICN) to 0.5% with PBS (0.5% BSA/PBS) was dispensed at 300 mL/well for blocking to prevent non-specific reaction. Thereafter, the plate was stood at 37° C. for 1 hr, and the culture supernatant containing IFN-β antibody to be quantified was diluted 1/10, 1/100 with 0.5% BSA/PBS and dispensed at 50 µL/well. Similarly, a standard solution serially diluted from 1 µg/mL by 1/3 up to 152 ng/mL was dispensed at 50 µL/well and the plate was stood at 37° C. for 1 hr. Thereafter, horseradish-derived peroxidase-labeled human λ chain antibody (BIOSORCE) was diluted 5,000-fold with 0.5% BSA/PBS solution, dispensed at 100 µL/well and stood at 37° C. for 1 hr. As a color development solution, 0.006% $H_2O_2$-0.2M citrate buffer (pH 4.0), 6 mg/mL ABTS-$(NH_4)_2$ (Wako Pure Chemical Industries, Ltd.), and ultrapure water (Milli-Q water) were mixed at a ratio of 10:1:9 and the solution was dispensed at 100 µL/well. After 30 min, the absorbance was measured at a wavelength of 414 nm. Between the respective reactions, the plate was washed 3 times with a solution obtained by diluting polyethylene (20) sorbitan monolaurate (Tween 20; Wako Pure Chemical Industries, Ltd.) to a concentration of 0.05% with PBS. The right figure in FIG. 1 is a graph showing the results of the amount of λ chain produced by SC-01MFP cells. As for the amount of λ chain produced, the production amount of the antibody remarkably increased from day 3 after the start of the culture and thereafter, as compared to the control experiment when deacylated gellan gum was added at a concentration of 0.015%. The area of the graph obtained FIG. 1, left and right figures, was calculated by a trapezoid method, and the area obtained from the graph of antibody production amount was divided by the area obtained from the graph of cell number (area obtained from graph of antibody production amount/area obtained from graph of cell number equivalent amount of antibody production per 1 cell) and a comparison thereof is shown in FIG. 2 (converted to ratio of addition of 0.015% deacylated gellan gum relative to control as 1). By the addition of deacylated gellan gum, λ chain production amount per 1 cell increased about 3-fold.

Example 2

Sample

The host cell strain used in this Example is Chinese hamster ovary-derived cell line CHO-K1 (ATCC CCL-61 (trademark)). For the evaluation of substance producibility, human interferon β (IFN-β) gene was incorporated into CHO-K1, and IFN-β-producing cell line was prepared in the culture supernatant, as shown below.

First, IFN-β gene was obtained from human skin-derived normal diploid fibroblast strain TIG-108, which is an IFN-β-producing cell. TIG-108 ($5×10^6$ cells) was centrifuged at 400×g for 5 min, and the supernatant was removed. A nucleic acid extraction reagent ISOGEN (NIPPON GENE CO., LTD., 1 mL), and chloroform (Wako Pure Chemical Industries, Ltd., 0.2 mL) were added to allow precipitation of DNA, protein in the organic layer. After centrifugation at 12000×g for 15 min, the aqueous phase (RNA layer) was obtained, isopropanol (Wako Pure Chemical Industries, Ltd., 0.5 mL) was added, and the mixture was centrifuged at 12000×g for 15 min to allow precipitation of RNA. The precipitated RNA was dissolved in sterile water, First-Stand Reaction Mix Beads (Amersham Biosciences) and pd(N)6 Randam Hexamer (Amersham Biosciences, 1 µL) were added, and the mixture was stood at room temperature for 1 min and subjected to reverse transcription at 37° C. for 60 min to synthesize cDNA.

Then, amplification of IFN-β gene by PCR was tried. First, sterile water (35.5 µL), Blend Taq buffer (5 µL), dNTP mix (4 µL), Primer F (5'-ATGACCAACAAGTGTCTCCT-3'; SEQ ID NO: 1) (1 µL, 10 pmoles), Primer R (5'-TCAGTTTCGGAGGTAACCTG-3"; SEQ ID NO: 2) (1 µL, 10 pmoles), Taq DNA polymerase (0.25 µL, Takara Bio Inc.), and cDNA (3 µL, 50 ng) were mixed in a 0.2 mL tube. The tube was placed in a Program Temp. Control System (ASTEC CO., LTD.) and PCR was performed. The PCR product was confirmed by 1% agarose gel electrophoresis, and purified by Freeze'N Squeese spin column (BIO RAD Laboratories Inc.). The purified PCR product (2 µL) and pTARGET vector (1 µL, 50 ng) were mixed with TaKaRa DNA Ligation Kit (Takara Bio Inc., 3 µL), and the mixture was subjected to a ligation reaction at 16° C. for 30 min. Then, pTARGET vector after ligation was introduced into JM109 cells (Promega) by a heat shock reaction, plated on an LB medium plate. Grown colonies were obtained, subjected to shaking culture in an LB medium (1 mL) at 37° C. overnight, and the pTARGET vector was extracted using a QIA prep Spin Miniprep Kit (QIAGEN). Then, the pTARGET vector was cleaved with restriction enzyme PstI (TOYOBO CO., LTD.) having a recognition sequence on the IFN-β gene sequence, whereby cloning of IFN-β gene by pTARGET vector was confirmed.

Then, the CHO-K1 cell line was cultured in a 10% fetal bovine serum (Fetal bovine serum FBS, Trace)-containing-E-RDF (10% FBS-E-RDF) medium, adjusted to $5×10^6$ cells/mL and the medium was exchanged with PBS. Then, cloning of IFN-β gene to the pTARGET vector was confirmed.

The gene (3 µg) was added, and a voltage was charged under the conditions of 0.75 kV/cm, 350 µF. Recovery culture was performed in 10% FBS-E-RDF medium, the cells were dispensed to a 96 well culture plate (Beckton & Dickinson) at 100 µL/well. After incubation for 24 hr, transgenic cells were selected and cultured in 10% FBS-E-RDF medium containing G-418 (Geneticin, Invitrogen) at a final concentration of 500 µg/mL. The cells with confirmed growth were confirmed for IFN-β gene expression, whereby IFN-β-producing CHO-K1 cells were prepared.

[Deacylated Gellan Gum Culture Evaluation System]

Figure 3:
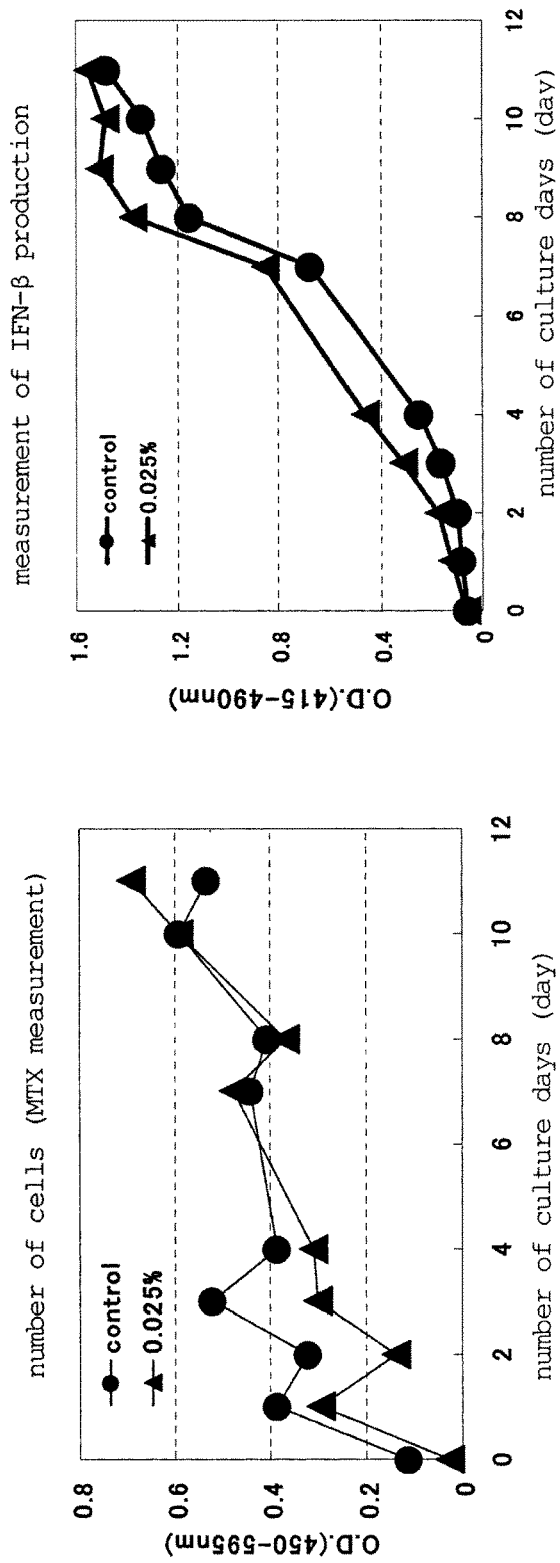
FIG. 3 shows comparison of cell number increase and IFN-β production amount when Chinese hamster ovary-derived cell line (CHO-K1) obtained by incorporating human interferon β (IFN-β) gene into CHO-K1 was cultured in the presence of deacylated, gellan gum (0.025%) and in the absence thereof (control).
Figure 4:
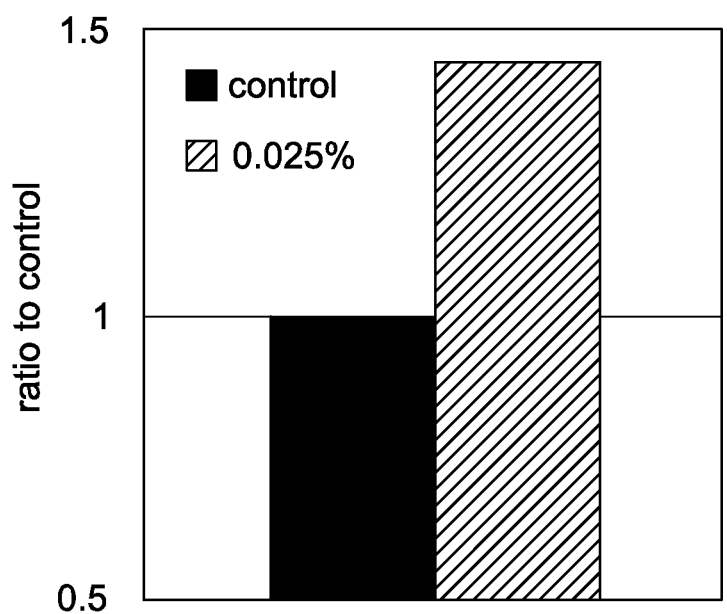
FIG. 4 shows comparison of IFN-β production amount area under graph in the presence of deacylated gellan gum (0.025%) and that of control as 1, wherein the IFN-β production amount area under graph was amended using the cell number increase area under graph obtained by calculating, by a trapezoid method, the area under graph of the cell number increase (left FIG. and IFN-β production amount (right figure) when CHO-K1 was cultured in the presence of deacylated gellan gum (0.025%) and in the absence thereof (control), in the test using CHO-K1 described in FIG. 3, (IFN-β production amount area under graph/cell number increase area under graph).

Deacylated gellan gum powder (KELCOGEL CG-LA, manufactured by SANSHO Co., Ltd.) was dissolved in ultrapure water (Milli-Q water) at 4 g/L. The solution was warmed in hot water and, after confirmation of dissolution of deacylated gellan gum powder, sterilized by autoclave. The sterilized aqueous deacylated gellan gum solution was stood still and allowed to cool to room temperature, and, as serum-free medium, a mixed medium containing deacylated gellan gum at a concentration of 0.025% relative to E-RDF medium (manufactured by KYOKUTO PHARMACEUTICAL INDUSTRIAL CO., LTD.) containing insulin (bovine-derived, final concentration: 5 µg/mL), transferrin (bovine-derived, final concentration: 20 µg/mL), ethanolamine (final concentration: 20 µmol) and sodium selenite (final concentration: 25 nmol) was prepared. For a control group, the above-mentioned serum-free E-RDF medium (manufactured by KYOKUTO PHARMACEUTICAL INDUSTRIAL CO., LTD.) without deacylated gellan gum was used. Then, the cells were plated on a 96 well immunoplate by 100 µL, to $1×10^4$ cells/well in the prepared medium. Every 24 hr, Cell Counting Kit8 (manufactured by DOJINDO LABORATORIES) was added at 10 µL/well and the mixture was incubated for 1.5 hr. The culture medium (100 µL) was transferred to another 96 well plate, and the absorbance was measured at 450-595 nm. As a result, as shown in FIG. 3, left figure, it was found that the deacylated gellan gum-added culture system does not influence the cell proliferation effect in a serum-free E-RDF medium (manufactured by KYOKUTO PHARMACEUTICAL INDUSTRIAL CO., LTD.) as compared to the culture system free of addition.

[Measurement of IFN-β Production Amount by Enzyme Antibody Method]

The amount of IFN-β produced in the above-mentioned culture supernatant was measured by an enzyme antibody method (ELISA; enzyme-linked immunosorbent assay). Goat anti-human IFN-β antibody (R&D System INC.) was diluted to 1 μg/mL with phosphate buffered saline (PBS) and dispensed to a 96 well immunoplate at 100 μL/well to coat the plate. After standing at 37° C. for 1 hr, a solution obtained by diluting bovine serum albumin (BSA; ICN) to 0.5% with PBS (0.5% BSA/PBS) was dispensed at 300 μL/well for blocking to prevent non-specific reaction. Thereafter, the plate was stood at 37° C. for 1 hr, and the culture supernatant containing IFN-β antibody to be quantified was diluted 1/10 with 0.5% BSA/PBS and dispensed at 50 μL/well. Similarly, 0.33 μg/mL standard solution was dispensed at 50 μL/well and the plate was stood at 37° C. for 1 hr. Thereafter, mouse anti-human IFN-β antibody (R&D System INC.) was diluted with 0.5% BSA/PBS to 1 μg/mL, dispensed at 100 μL/well, and the plate was stood at 37° C. for 1 hr. Thereafter, horseradish-derived peroxidase-labeled goat anti-mouse IgG antibody was diluted 5,000-fold with 0.5% BSA/PBS solution, dispensed at 100 μL/well, and the plate was stood at 37° C. for 1 hr. As a color development solution, 10% 3,3',5,5'-tetramethylbenzidine (TMB)-dimethyl sulfoxide (DMSO) solution/0.006% $H_2O_2$-0.2M citrate buffer (pH 4.0) solution was dispensed at 100 μL/well, the reaction was quenched 30 min later with $1N-H_2SO_4$ solution, the absorbance was measured at a wavelength of 450 nm. Between the respective reactions, the plate was washed 3 times with a solution obtained by diluting polyethylene (20) sorbitan monolaurate (Tween 20; Wako Pure Chemical Industries, Ltd.) to a concentration of 0.05% with PBS. The left figure in FIG. 3 is a graph showing the time-course changes of cell number and the right figure is a graph showing the time-course changes of IFN-β production amount by CHO-K1 cells. As shown in FIG. 3, right figure, the IFN-β production amount increases in a serum-free culture by the addition of 0.025% deacylated gellan gum, as compared to those without addition. The area of the graph obtained FIG. 3, left and right figures, was calculated by a trapezoid method, and the area under graph obtained from the graph of IFN-3 was divided by the area under graph obtained from the graph of cell number (area obtained from graph of IFN-β/area obtained from graph of cell number ≈ equivalent amount of IFN-β production per 1 cell) and a comparison thereof is shown in FIG. 2 (converted to ratio of addition of 0.025% deacylated gellan gum relative to control as 1). By the addition of deacylated gellan gum, IFN-β production amount per 1 cell increased by about 44%.

Example 3

Sample

The cell line used in this Example is CHO-K1 cell line incorporating the human interferon β gene used in Example 2, which produces human interferon β in the culture supernatant.

[Means of Micronization of Gel Tissue]

Deacylated gellan gum powder (KELCOGEL CG-LA, manufactured by SANSHO Co., Ltd.) was dissolved in ultrapure water at 1 g/100 mL. The solution was sterilized and gel was dissolved by autoclave.

Then, this gel subjected to 4 kinds of treatments using EDTA, potassium oxalate, UV and ultrasonication, to achieve physicochemical micronization, and an influence on the cell proliferation and production amount of the cell product was examined.

First, EDTA (manufactured by DOJINDO LABORATORIES, 0.1 g) was dissolved in 500 mL of phosphate buffered saline (PBS) and, after autoclave sterilization, equal amounts of gel and EDTA solution were mixed and stood at room temperature for 1 day.

Thereafter, a liquid part and a gel part were separated by centrifugation at 4000×g, 10 min. The gel part was added at 5% (w/v) and cultured in 5% fetal bovine serum-containing ERDF medium (manufactured by KYOKUTO PHARMACEUTICAL INDUSTRIAL CO., LTD.).

As for potassium oxalate (manufactured by Wako Pure Chemical Industries, Ltd.), a 5% potassium oxalate solution was prepared with ultrapure water and, after filter sterilization, equal amounts of gel and potassium oxalate solution were mixed and stood at room temperature for 1 day. A liquid part and a gel part were separated by centrifugation at 4000×g, 10 min, and the gel part was added at 5% (w/v) and cultured in 5% fetal bovine serum-containing ERDF medium (manufactured by KYOKUTO PHARMACEUTICAL INDUSTRIAL CO., LTD.).

As for UV, a gel solution was placed at a distance of 55 cm from a commercially available 15 W UV lamp, and UV was irradiated overnight. The sample was added at 5% (w/v) and cultured in 5% fetal bovine serum-containing ERDF medium (manufactured by KYOKUTO PHARMACEUTICAL INDUSTRIAL CO., LTD.).

Finally, ultrasonication was applied to the gel solution at output power 20 W, frequency 28 KHz for 5 min, and added at 5% (w/v) and cultured in 5% fetal bovine serum-containing ERDF medium (manufactured by KYOKUTO PHARMACEUTICAL INDUSTRIAL CO., LTD.).

As a control group, 5% fetal bovine serum-containing ERDF medium (manufactured by KYOKUTO PHARMACEUTICAL INDUSTRIAL CO., LTD.) without gel was used.

Also, finally, two patterns of with and without vigorous pipetting with a pipette in an attempt to avoid recoagulation of the gel were performed when adding each gel sample after EDTA, potassium oxalate, UV, ultrasonication to a culture medium.

Figure 5:
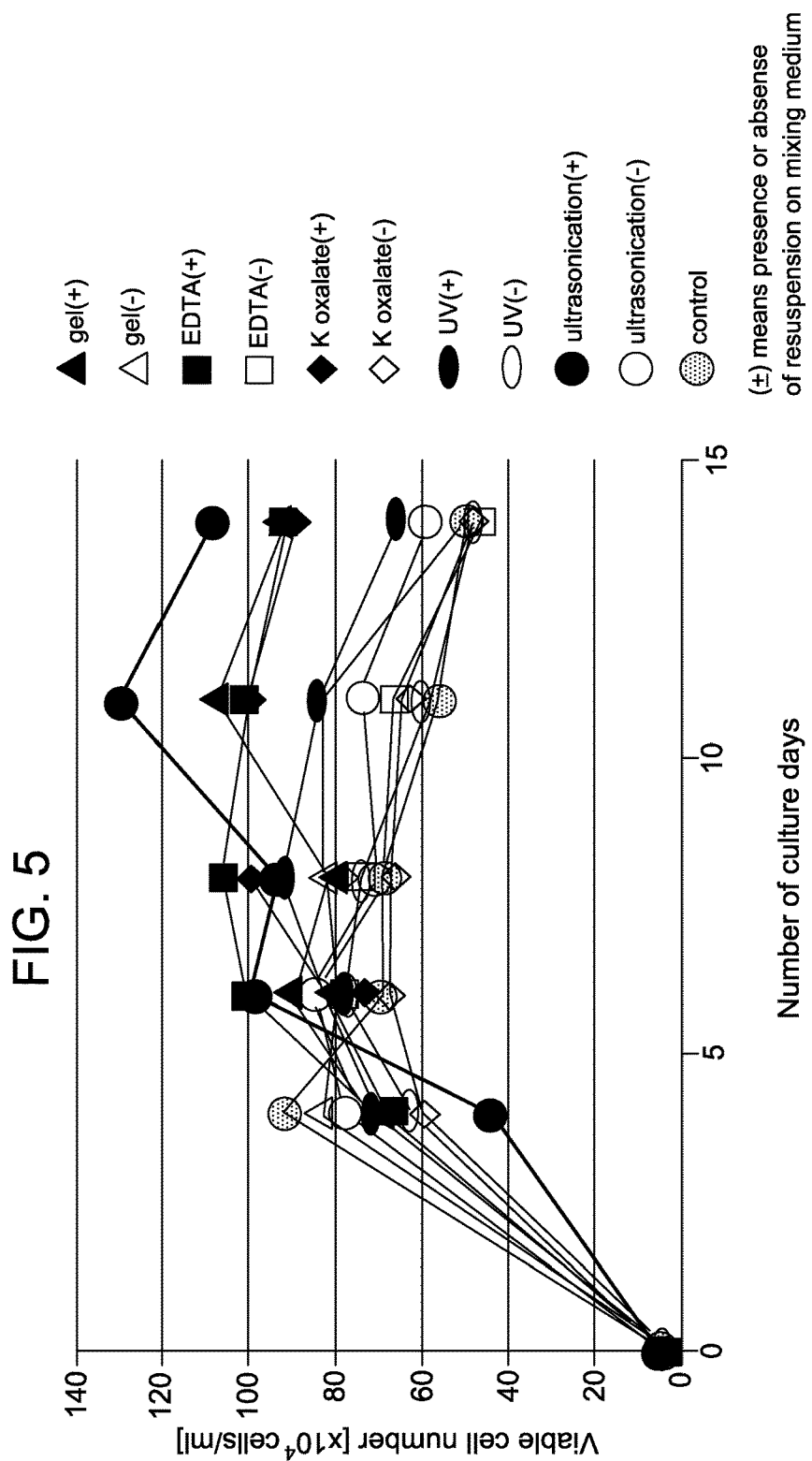
FIG. 5 shows an effect of a gel micronization treatment on cell proliferation when the gel was ultrasonicated and resuspended when added to the culture medium.

The cells were plated on a 24 well culture plate by 1 mL to achieve 1×10⁵ cells/well in the prepared culture medium containing gel after each treatment. The cell number during culture was measured by a hemocytometer. As a result, as shown in FIG. 5, a clearly higher growth supporting activity than cell proliferation of the control and other samples was observed on day 7 and thereafter of culture when the gel was ultrasonicated and resuspended upon addition to a culture medium.

[Measurement of IFN-β Production Amount by Enzyme Antibody Method]

The measurement method is the same as in Example 2.

Figure 6:
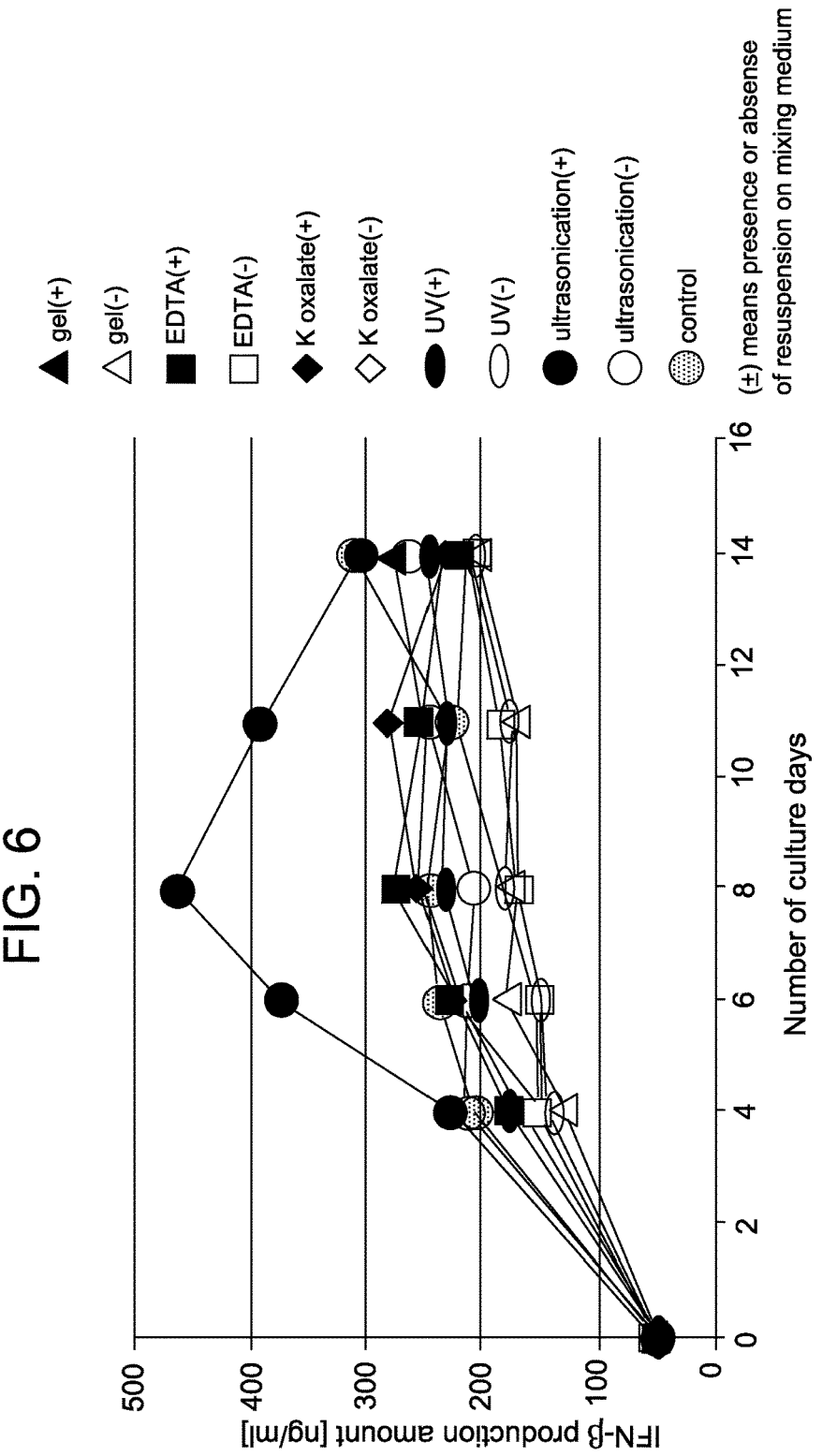
FIG. 6 shows an effect of a gel micronization treatment on IFN-β production of cells when the gel was ultrasonicated and resuspended when added to the culture medium.

As shown in FIG. 6, a remarkably higher interferon β production amount than that of the control and other samples was observed on day 6 and thereafter of culture when the gel was ultrasonicated and resuspended upon addition to a culture medium.

Example 4

Sample

The cell line used in this Example is CHO-K1 cell line incorporating the human interferon β gene used in Example 2, which produces human interferon β in the culture supernatant.

[Deacylated Gellan Gum Culture Evaluation System]

Deacylated gellan gum powder (KELCOGEL CG-LA, manufactured by SANSHO Co., Ltd.) was dissolved in ultrapure water at 1 g/100 mL. The solution was sterilized and gel was dissolved by autoclave. The gel was added to 5% fetal bovine serum-containing ERDF medium (manufactured by KYOKUTO PHARMACEUTICAL INDUSTRIAL CO., LTD.) at 5% (w/v), and the mixture was dispensed by 200 mL to a glass roller bottle (manufactured by WHEATON) and a polystyrene roller bottle (manufactured by BD), and cultured. The both roller bottle incubator had a surface area of about 850 cm$^2$.

The density of the cells plated was adjusted to $1 \times 10^5$ cells/well.

The control was the cells cultured only in 5% fetal bovine serum-containing ERDF medium (manufactured by KYOKUTO PHARMACEUTICAL INDUSTRIAL CO., LTD.) free of gel.

The rotating speed of the roller was set to 1 rpm.

Figure 7:
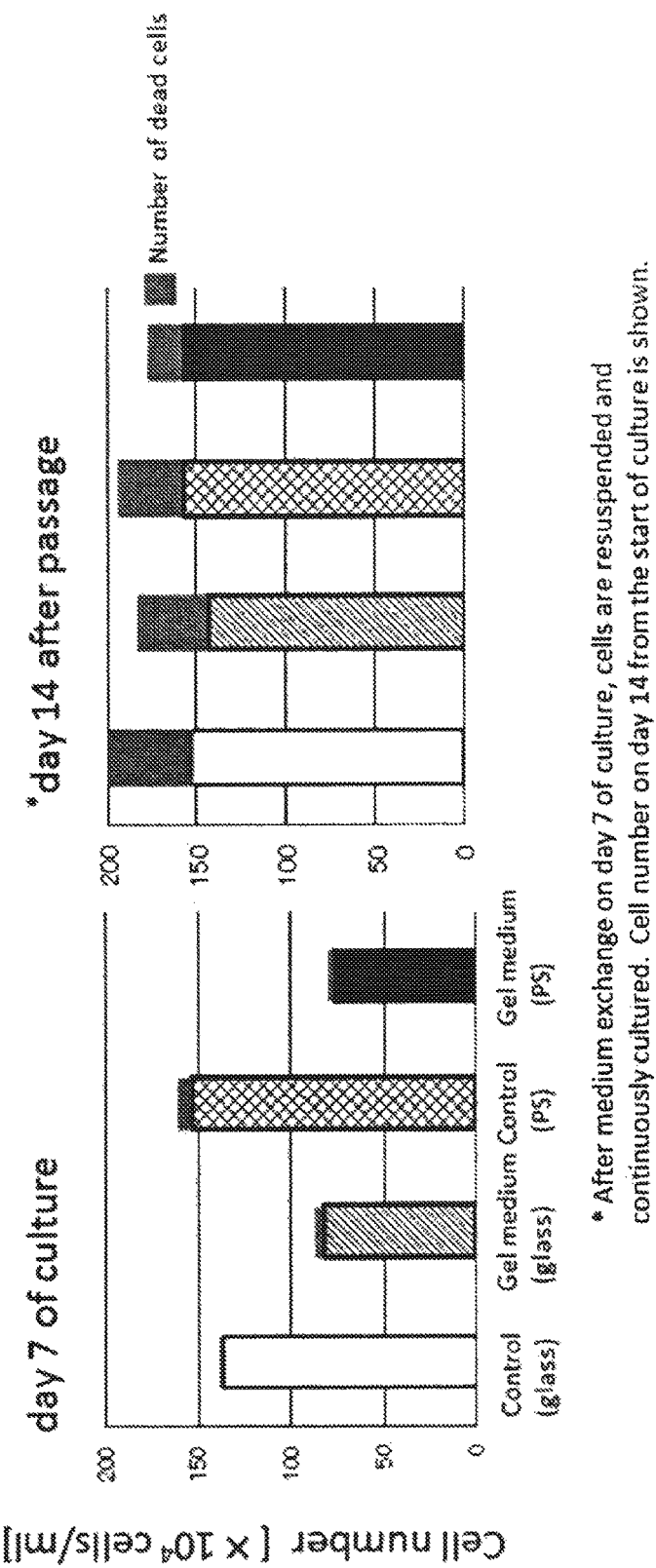
FIG. 7 shows an effect of the difference in the material of a roller bottle on the cell-proliferating potency in gel.

After start of the culture of the roller bottle, respective cells were recovered by centrifugation at 1600×g for 5 min on day 7, and passaged by resuspending in the same medium as used when the culture was started, and the cells were cultured until day 14. The cell number was measured by a hemocytometer. FIG. 7 shows changes in the cell number and survival rate before and after the passage on day 7 of culture. As a result, all cells showed an increase in the cell number after the passage, but the survival rate was somewhat lower in glass.

[Measurement of IFN-β production amount by enzyme antibody Method]

The enzyme antibody method for the amount of IFN-β produced in the culture supernatant was the same as that described in Example 2.

FIG. 8 shows difference in the interferon 3 production amount depending on the material of the roller bottle (made of glass or polystyrene). Before passage and on day 7 of culture, the experiment system using gel added in a glass roller bottle showed a somewhat lower IFN-3 production amount, but other systems did not show much difference in the IFN-β production amount. On the other hand, after culture following the passage on day 7 from the start of the culture, the system using gel added in a polystyrene roller bottle showed a remarkably improved IFN-β production amount, and the effect thereof reached about 1.5-fold that of the system without addition of the gel.

INDUSTRIAL APPLICABILITY

As described in detail in the above, using the medium additive for animal cell of the present invention, the production amount of a useful protein can be promoted.

Furthermore, since the production method of protein of the present invention can produce a desired protein still more efficiently, it is advantageous in the production cost and can greatly contribute to a mass supply of, for example, biopharmaceutical products such as antibody drugs and the like, and the like.

This application is based on U.S. provisional patent application No. 61/692,549 (filing date: Aug. 23, 2012), the contents of which are incorporated in full herein.

[Sequence Listing]
SEQUENCE LISTING

```
<110>  Nissan Chemical Industries, LTD.
       Institute of National Col-
       leges of Tech-
       nology, Japan
<120>  Enhancing ingredients for protein pro-
duction from various cells
<130>  202577
<150>  U.S. 61/692549
<151>  2012-08-23
<160>  2
<170>  PatentIn version 3.3
<210>  1
<211>  20
<212>  DNA
<213>  Artificial Sequence
<400>  1
atgaccaaca agtgtctcct                                    20
<210>  2
<211>  20
<212>  DNA
<213>  Artificial Sequence
<400>  2
tcagtttcgg aggtaacctg                                    20
```

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1
atgaccaaca agtgtctcct                                    20

<210> SEQ ID NO 2
<211> LENGTH: 20
<212> TYPE: DNA
<213> ORGANISM: Artificial Sequence
```

```
<220> FEATURE:
<223> OTHER INFORMATION: Synthetic Sequence

<400> SEQUENCE: 2
tcagtttcgg aggtaacctg                                              20
```

The invention claimed is:

1. A method of producing a protein by using an animal cell culture, comprising
   cultivating an animal cell in a medium comprising 0.01% to 0.05% (weight/volume) deacylated gellan gum in a culture tool,
   wherein the animal cell is a Chinese Hamster Ovary (CHO) cell, a human cancer cell, or a hybridoma, into which a gene encoding the protein has been introduced,
   wherein the protein is an immunity related protein, a protein relating to cell proliferation/differentiation, or a membrane protein,
   wherein the culture tool is composed of polystyrene,
   thereby producing the protein.

2. The method according to claim 1, wherein the animal cell is cultivated for at least period (a) or (b):
   (a) a part or all of the period when the animal cell to be cultivated can sufficiently grow,
   (b) a part or all of the period when the animal cell can sufficiently produce a desired protein.

3. The method according to claim 1, which increases production of the protein by the animal cell relative to production in the absence of deacylated gellan gum.

4. The method according to claim 3, which increases the production of the protein per 1 cell of the animal cell relative to production in the absence of deacylated gellan gum.

5. The method according to claim 1, wherein the animal cell is cultured in the further presence of at least one component selected from the group consisting of amino acids, vitamins, energy sources, osmoregulators, iron sources, and pH buffers.

6. The method according to claim 1, wherein the protein is an antibody or a cytokine.

7. The method according to claim 1, wherein the medium comprises serum.

8. The method according to claim 7, wherein the medium comprises serum at a concentration of not less than 1% (w/v) and not more than 15% (w/v).

9. The method according to claim 1, wherein the medium comprises a serum alternative.

10. The method according to claim 9, wherein the medium comprises a serum alternative at a concentration of not less than 1% (w/v) and not more than 15% (w/v), and wherein the serum alternative is selected from the group consisting of a plasma protein, a hormone, a growth factor, and a salt.

11. A method of increasing the production of a protein produced by an animal cell in a culture medium, comprising
    cultivating an animal cell in a medium comprising 0.01% to 0.05% (weight/volume) deacylated gellan gum in a culture tool,
    wherein the animal cell is a Chinese Hamster Ovary (CHO) cell, a human cancer cell, or a hybridoma, into which a gene encoding the protein has been introduced,
    wherein the protein is an immunity related protein, a protein relating to cell proliferation/differentiation, or a membrane protein,
    wherein the culture tool is composed of polystyrene,
    thereby increasing the production of the protein relative to production in the absence of deacylated gellan gum.

12. The method according to claim 11, which increases the production of the protein per 1 cell of the animal cell relative to production in the absence of deacylated gellan gum.

13. The method according to claim 11, wherein animal cell is cultured in the further presence of at least one component selected from the group consisting of amino acids, vitamins, energy sources, osmoregulators, iron sources, and pH buffers.

14. The method according to claim 11, wherein the protein is an antibody or cytokine.

15. The method according to claim 11, wherein the medium comprises serum.

16. The method according to claim 15, wherein the medium comprises serum at a concentration of not less than 1% (w/v) and not more than 15% (w/v).

17. The method according to claim 11, wherein the medium comprises a serum alternative.

18. The method according to claim 17, wherein the medium comprises a serum alternative at a concentration of not less than 1% (w/v) and not more than 15% (w/v), and wherein the serum alternative is selected from the group consisting of a plasma protein, a hormone, a growth factor, and a salt.

* * * * *